United States Patent [19]

Horlenko et al.

[11] Patent Number: 4,665,216

[45] Date of Patent: May 12, 1987

[54] PROCESS FOR PRODUCING N-ACYL-ACYLOXY AROMATIC AMINES

[75] Inventors: Theodore Horlenko, Corpus Christi; James H. George, Portland, both of Tex.

[73] Assignee: Celanese Corporation, New York, N.Y.

[21] Appl. No.: 710,787

[22] Filed: Mar. 12, 1985

[51] Int. Cl.$^4$ .................................. C07C 69/017
[52] U.S. Cl. .................................. 560/142; 560/144
[58] Field of Search .................................. 560/142, 144

[56] References Cited

U.S. PATENT DOCUMENTS

| 2,650,933 | 9/1953 | Pearl et al. | 564/259 |
| 2,833,825 | 5/1958 | Lewis | 260/142 |
| 4,507,248 | 3/1985 | Mathew et al. | 564/259 |
| 4,560,789 | 12/1985 | Davenport | 560/142 |
| 4,568,763 | 2/1986 | Davenport | 569/142 |

FOREIGN PATENT DOCUMENTS 2616986 10/1977 Fed. Rep. of Germany ...... 260/142

OTHER PUBLICATIONS

Ganboa, "Synthesis Communications", vol. 13 (11), pp. 941–944 (1983).
Hawley, "The Condensed Chemical Dictionary", 8th Ed., Reinhold Co. (1974).
Stephen et al, (I) J. Chemical Society", (1931), pp. 886–895.
Stephen et al, (II) J. Chemical Society", (1956), pp. 980–985.
Bazkert, "Chemical Abstracts", vol. 94: 208934f.
Mostowicz et al, "Chemical Abstracts", vol. 91: 157234f
Auwers et al, Chemishe Berichte, 58, 36–51 (1925).
Pearson et al, J. Amer. Chem. Soc., 75, 5905–5908. (1953).
Simons et al, (I), J. Amer. Chem. Soc., 61, 1795–6, (1939).
Simons et al, (II), J. Amer. Chem. Soc., 62, 485–6, (1940).
Dann and Mylius, Annalen der Chemie, 587 Band, 1–11 (1954).

*Primary Examiner*—Warren B. Lone
*Attorney, Agent, or Firm*—R. F. Green; D. R. Cassady

[57] ABSTRACT

A process is provided for producing N-acyl-acyloxy aromatic amine, such as 4-acetoxyacetanilide by reacting a hydroxy-aromatic ketoxime with a carboxylic acid anhydride, e.g. acetic anhydride, in the presence of phosphoric or oxalic acid as a Beckmann rearrangement catalyst. Preferably the ketoxime is prepared by reacting a hydroxy aromatic ketone such as 4-hydroxyacetophone with a hydroxyl amine salt, and the ketone is obtained by the Fries rearrangement of a phenolic ester, e.g. phenyl acetate or the Friedel-Crafts acylation of a phenolic compound, e.g. phenol, with an acylating agent, e.g. acetic acid.

17 Claims, No Drawings

PROCESS FOR PRODUCING N-ACYL-ACYLOXY AROMATIC AMINES

FIELD OF THE INVENTION

This invention relates to a method for making N-acyl-acyloxy aromatic amines, such as 4-acetoxyacetanilide (AAA), from hydroxy aromatic ketones and their oximes, such as 4-hydroxyacetophenone oxime.

BACKGROUND OF THE INVENTION

It is known to produce N-acyl-acyloxy aromatic amines, e.g. 4-acetoxyacetanilide, by preparing the sodium salt of the corresponding N-acylhydroxy aromatic amine, e.g. N-acetyl-para-aminophenol (APAP), and reacting the sodium salt with the appropriate carboxylic acid anhydride, e.g. acetic anhydride. The N-acylhydroxy aromatic amine, e.g. APAP, used as the starting material for the foregoing reaction is in turn prepared by acylating the corresponding hydroxy aromatic amine, e.g. para-aminophenol, with an acylating agent such as an anhydride, e.g. acetic anhydride. However the latter reaction may cause problems such as the difficulty of mono-acylating the hydroxy aromatic amine, oligomerization of the hydroxy aromatic amine, and color body formation.

Furthermore, when APAP is produced from para-aminophenol, nitro-benzene typically is catalytically hydrogenated and concomitantly rearranged in the presence of a platinium catalyst to produce the para-aminophenol, presenting the problem of recovering the dissolved platinum catalyst.

It is also known to prepare APAP by hydrogenating 4-nitro-chlorobenzene to a 4-chloroaniline which is then reacted with aqueous KOH to form para-aminophenol. This is then acetylated as described previously to form the N-acetyl-para-aminophenol. This process is relatively complex requiring a fair number of reaction and purification steps. Moreover, the acetylation step in this process is believed to give rise to the same problems as occurs in the acetylation step of the nitrobenzene process described previously.

The preparation of hydroxy aromatic ketones by the Fries rearrangement of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Ganboa et al, Synthetic Communications 13(11), 941-944 (1983) show the production of acetanilide from acetophenone by refluxing in a solution of hydroxylamine hydrochloride. There is however no suggestion of the synthesis of N-acylacyloxy aromatic amines such as 4-acetoxyacetanilide (AAA) or of the synthesis of N-acylhydroxy aromatic amines such as N-acetyl-para-aminophenol (APAP).

The conversion of phenyl acetate or phenol and an acetylating agent, to 4-hydroxyacetophenone by a Fries rearrangement or Friedel-Crafts acetylation, respectively is shown in copending U.S. patent applications Ser. No. 616,989, filed June 4, 1984; Ser. No. 618,659, filed June 8, 1984 and now U.S. Pat. No. 4,524,217; Ser. No. 627,381, filed July 3, 1984 and now U.S. Pat. No. 4,560,789; Ser. No. 627,382, filed July 3, 1984 and now U.S. Pat. No. 4,568,763; Ser. No. 633,831, filed July 24, 1984; Ser. No. 633,832, filed July 24, 1984; and Ser. No. 642,981, filed Aug. 21, 1984, all owned by the same assignee as the present application. Previously there has been shown the conversion of 4-hydroxyacetophenone to the corresponding oxime, with the subsequent Beckmann rearrangement and accompanying acylation with a carboxylic acid anhydride to form an N-acyl-acyloxy aromatic amine. In such instances the specific Beckmann rearrangement catalysts were mineral acids such as sulfuric and hydrochloric acid; organic acids such a trifluoroacetic acid, para-toluenesulfonic acid, benzenesulfonic acid, and methane sulfonic acid; acidic ion-exchange resins such as Amberlyst ® 15 or Nafion ® 501 which are sulfonic acid ion-exchange resins produced by Rhom and Haas and Dupont, respectively; and thionylchloride.

SUMMARY OF THE INVENTION

The present invention provides a process for making an N-acyl-acyloxy aromatic amine of the formula:

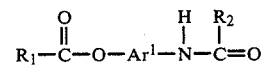

comprising reacting a hydroxy aromatic ketoxime having the formula:

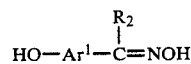

with a carboxylic acid anhydride having the formula:

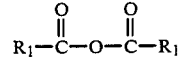

and a catalytic amount of phosphoric or oxalic acid, wherein in all instances $Ar^1$ represents a divalent aromatic radical, $R_1$ represents methyl, ethyl, propyl, or butyl, and $R_2$ represents a monovalent organic radical containing from 1 to about 18 carbon atoms.

The present invention thus avoids the need to use as catalysts strong acids such as sulfuric, para-toluenesulfonic acid, and methane sulfonic acid. Instead, relatively weak acids are employed. Phosphoric acid has a $K_a$ of $7.52 \times 10^{-3}$ while oxalic has a $K_a$ of $5.36 \times 10^{-2}$. Also, the use of phosphoric acid in particular results in high yields and/or superior product quality than with the use of the aforementioned strong acids.

DETAILED DESCRIPTION OF THE PREFERRED EMBODIMENTS

In accordance with the present invention, N-acyl-acyloxy aromatic amines, e.g. 4-acetoxyacetanilide (AAA), are produced by reacting a hydroxy aromatic ketone, e.g. 4-hydroxyacetophenone (4-HAP), with hydroxylamine or a hydroxylamine salt, to form the ketoxime of the ketone and subjecting the ketoxime to a Beckmann rearrangement and accompanying acylation by contacting the ketoxime with a carboxylic acid anhydride and a Beckmann rearrangement catalyst selected from the group consisting of phosphoric and oxalic acid, to form the N-acyl-acyloxy aromatic amine.

In another specific embodiment, 4-acetoxyacetanilide (AAA) is produced from phenyl acetate, or phenol and an acetylating agent such as acetic acid, by means of an integrated process including the steps of converting the phenyl acetate, or phenol and an acetylating agent, to 4-hydroxyacetophenone by a Fries rearrangement of Friedel-Crafts acetylation respectively, and converting the 4-hydroxyacetophenone to the corresponding ketoxime with hydroxylamine or a hydroxylamine salt. The ketoxime is then subjected to a Beckmann rearrangement and accompanying acetylation by contacting the ketoxime with acetic anhydride and a Beckmann rearrangement catalyst selected from the group consisting of phosphoric and oxalic acid, to form the 4-acetoxyacetanilide.

When carrying out the process of this invention using phenyl acetate as the starting material, the initial Fries rearrangement to produce 4-hydroxyacetophenone (4-HAP) from phenyl acetate is defined by equation (I):

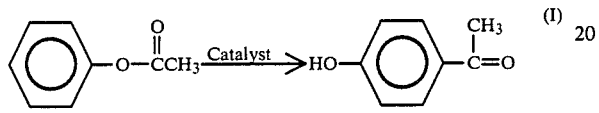

If phenol and an acetylating agent are used as the staring material, the resulting acetylation reaction to form 4-HAP is indicated by equation (II):

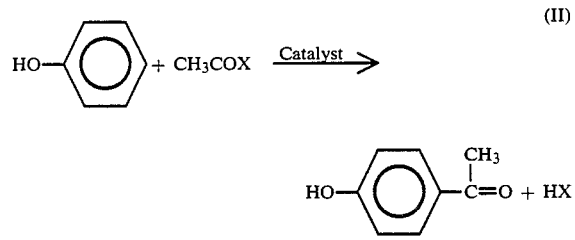

where X is the residue minus an acetyl group of compounds which are known acetylating agents. X may be, for example, hydroxy, acetoxy, or halide including fluoride, chloride, bromide, or iodide. Acetylating agents which may be used are for example, acetic acid, acetic anhydride, acetyl fluoride, acetyl chloride and acetyl bromide.

The ketoxime formation of this invention proceeds as indicated in equation (III):

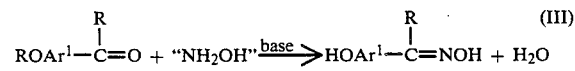

The formation of the ketoxime of 4-HAP, i.e. 4-HAP oxime, proceeds as in equation (IV):

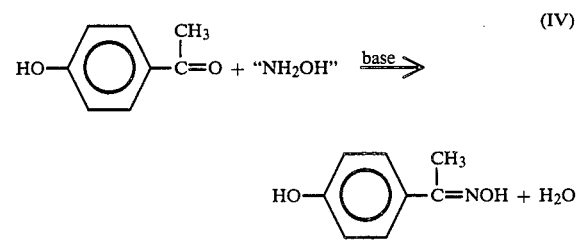

The Beckmann rearrangement and accompanying acylation of this invention proceeds as in equation (V):

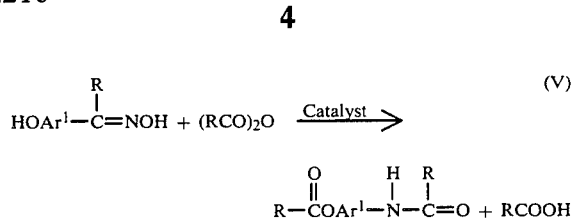

while the Beckmann rearrangement and accompanying acetylation when AAA is the desired product proceeds as in equation (VI):

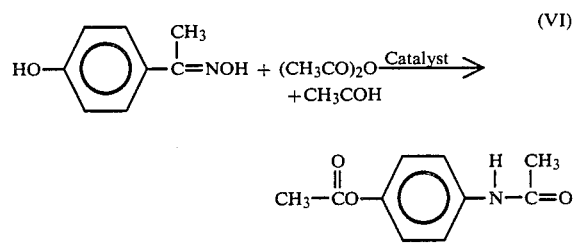

In equations (III) and (V), $Ar^1$ is a divalent aromatic radical. The specific nature of the radical is not critical but it is preferably a radical resulting from the removal of two ring hydrogen atoms from benzene, naphthalene, or biphenyl, either unsubstituted or with ring hydrogens substituted with radicals such as alkyl, alkenyl, alkynyl, alkoxy or acyloxy containing 1 to 18 carbon atoms, aralkyl containing 7 to 18 carbon atoms; halogen, e.g. chlorine, bromine, or iodine; hydroxy; amino; or sulfhydryl. $Ar^1$ is preferably 1,4-phenylene, 2,1-naphthylene, 2,6-naphthylene, 5-phenyl-1,2-phenylene, 3-phenyl-1,4-phenylene or 3-methyl-1,4-phenylene with the ketocarbon and corresponding groups occupying the first stated numbered position of $Ar^1$ when the positions are not equivalent. Most preferably $Ar^1$ is 1,4-phenylene.

The R groups in the foregoing equations may be the same or different and are each a monovalent organic radical containing, for example 1 to 18 carbon atoms preferably 1 to 4 carbon atoms. R may be, for example, alkyl, alkenyl, alkynyl, alkoxy, acyl or acyloxy containing 1 to 18 carbon atoms, either unsubstituted or substituted with radicals such as halogen, e.g. chlorine, bromine, or iodine; hydroxy; amino; sulfhydryl; or an aryl radical, Ar which may be a monovalent radical corresponding to the definition of $Ar^1$ given above except that the carbon bonded to OH is bonded to a hydrogen instead. Preferably, R is the same in all occurrences in equations (III) and (V) and is methyl, ethyl, propyl, or n-butyl and most preferably methyl corresponding to the use of acetate esters and methyl ketones in the latter equations. The preferred specific hydroxy aromatic ketone used to form the oxime is 4-hydroxyacetophenone (4-HAP) and the preferred product is 4-acetoxyacetanilide (AAA).

The hydroxy aromatic ketone used to form the oxime may be prepared by any method known in the art. For example, it may be prepared by the Fries rearrangement of the corresponding aromatic ester as indicated by the following equation, which is a generalized form of equation (I), where Ar, $Ar^1$ and R have the definitions given above:

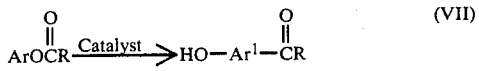

(VII)

Alternatively, a phenolic compound and an acylating agent may be reacted in a Friedel-Crafts acylation to form the hydroxy aromatic ketone, in accordance with the following equation, which is a generalization form of equation (II):

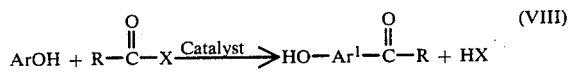

(VIII)

where Ar, Ar$^1$ and R have the meanings given previously and X is the residue minus the acyl group,

of the compounds which are known acylating agents, such as hydroxy, acyloxy, e.g. acetoxy, and halide, e.g. fluoride, chloride, bromide, and iodide. Examples of phenolic compounds which may be employed are phenol, 1-naphthol, 2-naphthol, 2-phenylphenol, 4-phenylphenol and o-cresol. Acylating agents which may be used are for example alkanoic acids, e.g. acetic and propionic acids, alkanoic acid anhydrides, e.g. acetic and propionic anhydrides, and acyl halides, e.g. acetyl and propionyl fluorides, chlorides, and bromides. Note that although the reaction of a phenolic compound and an acylating agent is characterized herein as a "Friedel-Crafts acylation," no opinion as to the mechanism of reaction should be implied by this characterization.

The catalyst for both of the foregoing reactions is preferably hydrogen fluoride but any other catalyst known in the art to be effective for the Fries and Friedel-Crafts reactions may be used, e.g. aluminum chloride, zinc chloride, or boron trifluoride.

In carrying out the reaction, the aromatic ester or phenolic compound and acylating agent, catalyst and if desired when an aromatic ester is the starting material, an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at a pressure, for example, of about 50 to about 500 psia (3.4 to 34 bar). If HF is used as the catalyst it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles per mole of aromatic ester or phenolic compound initially present in the reaction zone. If AAA or APAP is the desired product of the reaction, the starting material if a Fries rearrangement is employed will be phenyl acetate while phenol and an acetylating agent such as acetic acid is the starting material if a Friedel-Crafts acylation is utilized. In both cases, the starting material is converted to 4-HAP which is in turn converted by the process of this invention to AAA or APAP.

The conversion of hydroxy aromatic ketones, e.g. 4-HAP, into N-acylacyloxy aromatic amines, e.g. AAA, is accomplished by first forming the ketoxime from the hydroxy ketone as indicated by equations (III) and (IV), by contacting the ketone with hydroxylamine or a hydroxylamine salt, e.g. hydroxylamine hydrochloride, hydroxylamine sulfate, hydroxylamine bisulfate, or hydroxylamine phosphate, and a base, e.g. ammonium hydroxide, potassium hydroxide, sodium hydroxide, or lithium hydroxide in an amount, for example, of 1 to 3 moles per mole of hydroxylamine, at a temperature, for example of 0° to 110° C. for a period, for example, of 1 to 4 hours. Any pressure may be used, e.g. 80 mm. of mercury to 10 atmospheres absolute (0.1 bar to 10.1 bar). The reaction is preferably carried out in an aqueous or alcoholic medium, i.e. in the presence of water and/or an alcohol such as methanol, ethanol, or isopropanol.

In accordance with the present invention, the ketoxime may be converted into the corresponding N-acylacyloxy aromatic amine by a Beckmann rearrangement and accompanying acylation as shown in equations (V) and (VI), by contacting the ketoxime with the appropriate carboxylic acid anhydride and phosphoric or oxalic acid as a Beckmann rearrangement catalyst at a temperature, for example of 0° to 118° C. for a period for example of 1 to 4 hours. As defined in the foregoing equations, any of a broad class of anhydrides may be used but the anhydride is preferably that of an alkanoic acid containing 2 to 4 carbon atoms, e.g. acetic anhydride, propionic anhydride, or n-butyric anhydride. The pressure is not critical and may be, for example, in the range of 80 mm. of mercury to 10 atmospheres absolute (0.1 to 10.1 bar). Again, any Beckmann rearrangement catalyst may be used, as discussed above. The reaction may be advantageously carried out in the presence of the glacial carboxylic acid corresponding to the anhydride employed in the reaction in an amount, for example up to 50% by weight of the anhydride. The total amount of glacial carboxylic acid is not critical but the total amount of anhydride or anhydride/acid mixture is such that the ketoxime concentration is in most cases in the range of about 2 to 50% by weight at the start of the reaction.

The following examples further illustrate the invention.

EXAMPLE 1

This example illustrates the preparation of 4-hydroxyacetophenone by the Fries rearrangement of phenyl acetate using hydrogen fluoride as catalyst.

To a 300 cc Hastelloy C autoclave was charged 40.8 g (0.3 mol) of phenyl acetate. The autoclave was sealed, immersed in a Dry Ice/isopropanol bath and cooled internally to −45° C., and evacuated to ca. 100 Torr (0.13 bar). Addition of 120 g (6.0 mol) of anhydrous hydrogen fluoride was performed in a manner such as that the internal temperature of the autoclave did not exceed 0° C. The internal pressure of the reactor was then adjusted to 0 psig (1.1 bar) with nitrogen. The contents of the autoclave were stirred and heated to 75° C. for 1 h. The hydrogen fluoride was vented over a 45 min period at ca. 45° C. The mixture was poured onto 25 g of ice and neutralized with 45% potassium hydroxide solution. The aqueous mixture was extracted with ethyl acetate. The organic fraction was then dried over anhydrous magnesium sulfate, filtered, and the solvent was removed on a rotary evaporator to yield 44.0 g of a dark green solid corresponding to 99.9% conversion of phenyl acetate and 94.3% selectivity to 4-hydroxyacetophenone.

EXAMPLE 2

This example illustrates the preparation of 4-hydroxyacetophenone by the Fries rearrangement of phenyl acetate using hydrogen fluoride as catalyst with acetic anhydride as additive.

To a 300 cc Hastelloy C autoclave were added 30.6 grams (0.3 mole) of acetic anhydride. The autoclave was cooled to $-50°$ C. and evacuated to 5 Torr (0.007 bar) whereupon 120 g (6.0 mole) of anhydrous hydrogen fluoride was transferred from a cylinder to the autoclave. After the transfer of hydrogen fluoride was completed, the internal temperature and the internal pressure of the autoclave was adjusted to $-50°$ C. and 1.1 bar using nitrogen, respectively. To the stirred autoclave was added 81.6 g (0.6 mol) of phenyl acetate at such a rate that the temperature of the mixture did not exceed $-23°$ C. Upon completion of phenyl acetate addition, the contents were warmed to 50° C. and stirred for 3 h during which time a pressure of ca. 40 psig (3.9 bar) was generated. At the end of the run, the hydrogen fluoride was vented through a caustic scrubber and the contents of the autoclave were poured onto ca. 30 g of ice. The pH of the mixture was adjusted to 6.5 using 45% potassium hydroxide and the mixture was then extracted with 75 ml of ethyl acetate (3×). The organic solution was dried over anhydrous magnesium sulfate, filtered, and the solvent was removed using a rotary evaporator.

The reaction proceeded with 98.1% conversion of phenyl acetate and with the following selectivities: phenol 1%, 4-hydroxyacetophenone (4-HAP) 82.3%; 2-hydroxyacetophenone (2-HAP) 4.3%; 3-hydroxyacetophenone (3-HAP) 0.1%; 4-acetoxyacetophenone (4-AAP) 3.8%; and 4-(4'-hydroxyphenyl)acetophenone (HPAP) 0.4%.

EXAMPLE 3

This example described the formation of 4-hydroxyacetophenone by the Fries rearrangement of phenyl acetate using hydrogen fluoride as catalyst and acetic acid as additive.

The procedure for Example 2 was repeated except that 18 grams (0.3 mole) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP 0; 2-HAP 5.8%; 4-AAP 0.3%; and HPAP 0.3%.

EXAMPLE 4

This example illustrates the preparation of 4-hydroxyacetophenone (4HAP) by the Friedel-Crafts acetylation of phenyl with acetic acid as the acetylating agent.

Phenol (9.4 g, 0.1 moles) and acetic acid (12.0 g, 0.2 moles) were charged to a 300 ml Hastelloy C autoclave at room temperature. The reactor was evacuated and cooled to $-20°$ C. HF (100 g, 5 moles) was then transferred into the reactor. The reactor was heated to 80° C. and maintained for 1 hour at reaction temperature. At the end of the reaction the reactor was cooled to 20° C. and the excess HF was vented to a KOH scrubber. Ethyl acetate was added to the contents of the reactor. The mixture was then neutralized with 45% aqueous KOH. The resulting organic phase was separated, dried over MgSO4 and evaporated to afford a yellow solid which contained 13.1 g (0.096 moles) of 4-HAP.

EXAMPLE 5

This example illustrates the formation of 4-hydroxyacetophenone oxime from 4-hydroxyacetophenone and hydroxylamine hydrochloride.

A solution was prepared by adding 13.6 g (0.1 mol) of 4-hydroxyacetophenone, 7.6 g (0.11 mol) of hydroxylamine hydrochloride, and 10 g of water to 40 mL of ethanol. To the solution was added 5.0 g of 30% ammonium hydroxide which was then heated at reflux for 2 h. The ethanol was removed on a rotary evaporator to yield a yellow oil. An extractive work-up afforded 15.1 g (99%) of 4-hydroxyacetophenone oxime.

EXAMPLE 6

This example illustrates the formation of 4-hydroxyacetophenone oxime from 4-hydroxyacetophenone and hydroxylamine sulfate.

A solution was prepared by adding 20.4 g (0.15 mol) of 4-hydroxyacetophenone and 13.0 g (0.08 mol) of hydroxylamine sulfate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 7

This example illustrates the formation of 4-hydroxyacetophenone oxime from 4-hydroxyacetophenone and hydroxylamine phosphate.

A solution was prepared by adding 20.4 g (0.15 mol) of 4-hydroxyacetophenone and 12.9 g (65.6 mmol) of hydroxylamine phosphate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 8

This example illustrates the formation of 4-acetoxyacetanilide (AAA) by the Beckmann rearrangement and accompanying acetylation of 4-hydroxyacetophenone oxime using phosphoric acid ($H_3PO_4$) as catalyst.

To a mixture of 100 g of glacial acetic acid, 50 g of acetic anhydride, and 3.6 g of 85% $H_3PO_4$, sparged with nitrogen for 30 minutes, was added 10 g of 4-hydroxyacetophenone oxime. The mixture was heated at reflux for 1 hour under a nitrogen atmosphere, then cooled to room temperature and neutralized with 13% $Na_2CO_3$. The mixture was evaporated to dryness using a rotary evaporator and the solid was dissolved in 200 g of boiling water. After hot filtration, the solution was allowed to cool and stand overnight. The ensuing white crystals were collected, washed with 20 mL of water, and dried in a vacuum oven (60° C./100 mm Hg (0.13 bar)) for 2 hours. Upon drying, 9.4 g (73.9%) of white crystalline plates of 4-acetoxyacetanilide having a melting point of 148°–150° C. was obtained. An additional 0.8 g of AAA and 1.5 g of N-acetyl-para-aminophenol (APAP) were reclaimed from the mother liquor.

EXAMPLE 9

The same general procedures as Example 8 was employed with the following exceptions. The amount of phosphoric acid was 1.25 g of 85% $H_3PO_4$ and nitrogen was sparged for an additional 30 minutes after the oxime was added. After the crude product was evaporated to dryness, 100 g of boiling water was used to dissolve the same, leaving a straw-colored lower layer. The upper layer was filtered hot, cooled to room temperature in two hours and again filtered to recover 5.8 g of crystals (m.p. 150°–151° C.). The straw-colored lower layer was dissolved in hot water, and 2.04 g of white crystals were recovered therefrom (m.p. 148°–9° C.). An additional 0.8 of AAA and 0.6 g of APAP were recovered from the filtrates.

EXAMPLE 10

The same general procedure as Example 8 was employed with the following exceptions. After the oxime addition, nitrogen was sparged for an additional 30 minutes. After the crude product was dissolved in the boiling water and filtered, it was cooled to room temperature and filtered. There were 8.9 g of white crystalline plates (m.p. 147°–9° C.) recovered, containing 0.5% APAP. The filtrate also contained 0.9 g of AAA and 1.2 g APAP, as determined by G.C. analysis.

EXAMPLE 11

The same procedure as Example 10 was employed except that there was used 6.0 g of 85% $H_3PO_4$. 9.1 g of dry white crystalline plates of AAA were recovered, having a melting point of 152°–4° C. The filtrate was again analytically determined to contain 1.2 g APAP and 0.9 g of AAA.

EXAMPLE 12

The same procedure as Example 10 was employed except that the crude product was evaporated to dryness using a rotory evaporator without prior neutralization with 13% $Na_2CO_3$. To the dried crude product, 150 ml of $H_2O$ was added and the solution refluxed for 1.25 h. The solution was cooled to room temperature, resulting in an amber colored solution with no crystals. To the solution, 11.1 ml of 13% $Na_2CO_3$ was added to neutralize the $H_3PO_4$. The solution was evaporated to dryness with a rotary evaporator and 100 g of $H_2O$, 2 g of charcoal and 2 g of Celite were added, the solution refluxed, filtered hot, and cooled to room temperature. No crystals resulted. No AAA was recovered as a result of this procedure because $H_3PO_4$ was not neutralized before the evaporation step.

EXAMPLE 13

The same procedure as Example 10 was employed with the following exceptions. 1.2 g of 85% $H_3PO_4$ was used and the hot filtered solution was allowed to stand for approximately 2 days, after which it was filtered and 9.8 g of off-white crystals were recovered, having a melting point of 140°–143° C. Analysis of the filtrate showed 0.53 g of AAA and 0.32 g of APAP to be present.

EXAMPLE 14

The same general procedure as Example 10 was employed with the following exceptions. 4.3 g of oxalic acid was used in place of the phosphoric acid. There was recovered 8.1 g of dried crystal plates having a melting point of 135°–142° C. The filtrate and wash was analyzed to contain an additional 1.0 g of AAA.

EXAMPLE 15 (COMPARATIVE)

The same procedure as Example 10 was employed with the following exceptions. 3.6 g of malonic acid was used in place of the phosphoric acid. After the hot filtration step, an oily brown residue remained on the filter paper and the filtrate was an oily brown color. No crystals were recovered.

EXAMPLE 16 (COMPARATIVE)

The same procedure as Example 10 was employed with the following exceptions. 3.2 g of malonic acid was used in place of phosphoric acid. An oily brown product was recovered on the filter paper with a yellow filtrate. Very few crystals were recovered.

The N-acyl-acyloxy aromatic amines of this invention, e.g. AAA, may also be hydrolyzed to form the corresponding N-acyl-hydroxy aromatic amine, e.g. N-acetyl-para-aminophenol (APAP) which is one of the most widely used over-the-counter analgesics. The following example illustrates this process:

EXAMPLE 17

A mixture of 5 g (25.9 mmol) of 4-acetoxyacetanilide (AAA), 1.4 g of 70% methanesulfonic acid, and 50 g of water was heated at reflux for 1 h. Upon cooling, white crystals formed. Analysis (GLC) of the crystals as well as the aqueous solution indicated 90% conversion of the AAA to N-acetyl-para-aminophenol (APAP).

We claim:

1. A process for making an N-acyl-acyloxy aromatic amine of the formula:

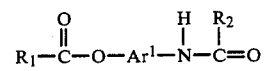

comprising reacting a hydroxy-aromatic ketoxime having the formula:

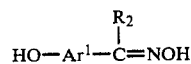

with a carboxylic acid anhydride having the formula:

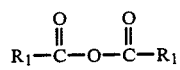

in the presence of a catalytic amount of phosphoric or oxalic acid, wherein $Ar^1$ represents a divalent aromatic radical, $R_1$ represents methyl, ethyl, propyl, or butyl, and $R_2$ represents a monovalent organic radical containing from 1 to about 18 carbon atoms.

2. The process of claim 1 wherein the reaction also occurs in the presence of a glacial carboxylic acid having the formula $R_1COOH$.

3. The process of claim 2 wherein the ketoxime is made by contacting a hydroxy aromatic ketone with a hydroxylamine salt and a base.

4. The process of claim 3 wherein said hydroxy aromatic ketone is 4-hydroxyacetophenone, said ketoxime is 4-hydroxyacetophenone oxime, said anhydride is acetic anhydride, and said N-acyl-acyloxy aromatic amine is 4-acetoxyacetanilide.

5. The process of claim 4 wherein said 4-acetoxyacetanilide is hydrolyzed to form N-acetyl-para-aminophenol.

6. The process of claim 3 also comprising contacting an ester of a phenolic compound and a carboxylic acid with a Fries rearrangement catalyst to form the hydroxy aromatic ketone.

7. The process of claim 6 wherein said Fries rearrangement catalyst is hydrogen fluoride.

8. The process of claim 7 wherein the ester is phenylacetate.

9. The process of claim 3 also comprising contacting a phenolic compound and an acylating agent with a Friedel-Crafts catalyst to form the hydroxy aromatic ketone.

10. The process of claim 9 wherein said Friedel-Crafts catalyst is hydrogen fluoride.

11. The process of claim 10 wherein the phenolic compound is phenol and the acylating agent is acetic acid.

12. The process of claim 2 carried out at a temperature of 0° to 118° C. and a pressure of 80 mm. of mercury to 10 atmospheres for a period of 1 to 4 hours, and wherein said glcial carboxylic acid is present in an amount up to 50% by weight of said anhydride and the concentration of said ketoxime is 2 to 50% by weight at the start of the reaction.

13. The process of claim 3 wherein said ketone is contacted with said hydroxylamine salt and 1 to 3 moles of said base per mole of hydroxylamine at a temperature of 0° to 110° C. and a pressure of 80 mm. of mercury to 10 atmospheres for a period of 1 to 4 hours.

14. The process of claim 7 wherein said ester is contacted with about 7 to 75 moles of hydrogen fluoride per mole of ester at a temperature of about 20° to 100° C. and a pressure of about 50 to 500 psia for a period of about ½ to 4 hours.

15. The process of claim 10 wherein said phenolic compound and acylating gent are contacted with about 7 to 75 moles of hydrogen fluoride per mole of phenolic compound at a temperature of about 20° to 100° C. and a pressure of about 50 to 500 psia for a period of about ½ to 4 hours.

16. The process of claim 1 wherein phosphoric acid is employed as the catalyst.

17. The process of claim 1 wherein oxalic acid is employed as the catalyst.

* * * * *